US007935508B2

(12) United States Patent
Schörken et al.

(10) Patent No.: US 7,935,508 B2
(45) Date of Patent: May 3, 2011

(54) PRODUCTION AND USE OF MONOGLYCERIDES

(75) Inventors: Ulrich Schörken, Düsseldorf (DE); Sabine Both, Neuss (DE); Frank Bongardt, Meerbusch (DE); Diana Stuhlmann, Düsseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 844 days.

(21) Appl. No.: 11/813,939

(22) PCT Filed: Jan. 10, 2006

(86) PCT No.: PCT/EP2006/000120
§ 371 (c)(1),
(2), (4) Date: Jul. 13, 2007

(87) PCT Pub. No.: WO2006/077022
PCT Pub. Date: Jul. 27, 2006

(65) Prior Publication Data
US 2008/0045606 A1 Feb. 21, 2008

(30) Foreign Application Priority Data
Jan. 19, 2005 (DE) .......... 10 2005 002 711

(51) Int. Cl.
*C12N 9/00* (2006.01)
(52) U.S. Cl. .......... 435/183; 435/252.1; 435/243
(58) Field of Classification Search .......... 435/252.1, 435/243, 183
See application file for complete search history.

(56) References Cited

U.S. PATENT DOCUMENTS

| | | | |
|---|---|---|---|
| 5,116,745 A | 5/1992 | Mazur et al. | |
| 5,316,927 A | 5/1994 | Zaks et al. | |
| 5,714,373 A * | 2/1998 | Stetter | 435/235.1 |
| 5,935,828 A | 8/1999 | Zaks et al. | |
| 6,905,850 B2 | 6/2005 | Irimescu et al. | |

FOREIGN PATENT DOCUMENTS

| | | |
|---|---|---|
| EP | 407959 | 1/1991 |
| EP | 0 721 492 | 7/1996 |
| EP | 1 300 470 | 4/2003 |
| FR | 2 772 391 | 6/1999 |
| JP | 60 102192 | 10/1985 |
| JP | 03 103499 | 4/1991 |
| JP | 03 108489 | 7/1991 |
| JP | 03 187385 | 8/1991 |
| WO | WO 90/04033 | 4/1990 |
| WO | WO 90 13656 | 11/1990 |
| WO | WO 91 16441 | 10/1991 |
| WO | WO 91/16442 | 10/1991 |
| WO | WO 95 03377 | 2/1995 |
| WO | WO 00 63322 | 10/2000 |
| WO | WO 01 19941 | 3/2001 |
| WO | WO 02 06505 | 1/2002 |
| WO | WO 2006/077023 | 7/2006 |

OTHER PUBLICATIONS

Uwe Bornscheuer, "Recent advances in the lipase-catalyzed biotransformation of fats and oils", Recent Res. Devel. Oil Chem., 3, 1999, pp. 93-106.
Hydrolases in Organic Synthesis, Wiley-VCH, 1999, eds. Bornscheuer & Kazlaukas (book).

* cited by examiner

*Primary Examiner* — Ruth A Davis

(57) ABSTRACT

A higher-yielding process for the production of monoglycerides in which triglycerides are enzymatically reacted with a catalytic amount of an esterase, preferably lipase, that has been activated by the addition of alkaline salts, in the presence of linear or branched alcohols containing 1 to 8 carbon atoms, then the esterase may be deactivated and it and the remaining alcohol removed, with the monoglycerides thus produced useful in lubricants, fuel additives, and emulsifying constituents in foods, and cosmetic and/or pharmaceutical formulations.

14 Claims, No Drawings

PRODUCTION AND USE OF MONOGLYCERIDES

CROSS-REFERENCE TO RELATED APPLICATIONS

This application is filed under 35 U.S.C. §371 claiming priority from application PCT/EP2006/00120 filed Jan. 10, 2006, which claims priority from German application DE 10 2005 002 711.3 filed Jan. 19, 2005; the entire contents of each application are incorporated herein by reference.

FIELD OF THE INVENTION

This invention relates generally to glycerides and, more particularly, to a process for the production of monoglycerides by enzymatic catalysis and to their use.

BACKGROUND AND RELATED ART

Enzymes are being increasingly used as catalysts in chemical and biochemical syntheses. Thus, in many cases, hydrolases, more especially lipases (EC 3.1.1.3), are already being used for lipolysis in industrial processes by virtue of the often relatively mild reaction conditions. These enzymes are produced by various microorganisms. To isolate the enzymes, fermentation of the microorganisms is followed by an expensive purification process. The effectiveness of these catalysts is often offset by the high costs of production and isolation, so that research groups are constantly striving to increase the yields of enzymes or the productivity of the enzymes.

The standard chemical method for producing monoglycerides involves the base-catalyzed glycerolysis of triglycerides, with a typical yield of 40 to 60% monoglyceride by weight, based on the weight of total glycerides in the final product. Further enrichment to a >90% monoglyceride content is achieved by physical separation techniques, such as molecular distillation or crystallization.

Various enzymatic routes suitable for the production of monoglycerides have been described in the literature: 1) enzymatic synthesis starting from fatty acid and glycerol; 2) enzymatic glycerolysis starting from triglyceride and glycerol which corresponds to the chemical process; 3) the 1,3-regioselective hydrolysis or alcoholysis of triglyceride. Summaries of these processes may be found, for example, in (a) Recent Rec. Devel. Oil Chem., 3(1999), 93-106; (b) Hydrolases in Organic Synthesis, Wiley-VCH (1999), eds. Bornscheuer & Kazlaukas.

Monoglycerides may only be enzymatically-synthesized effectively if water is removed from the reaction equilibrium, which removal is achieved by the addition of a molecular sieve or by a reaction in vacuo. In addition, solubilizers are required for a good synthesis (see Recent Res. Devel. Oil Chem., 3(1999)). Accordingly, the enzymatic synthesis of monoglycerides is not a cost-effective alternative to the chemical process. Enzymatic glycerolysis results in similar equilibrium adjustments to chemical glycerolysis for the production of monoglycerides. The synthesis of enriched monoglycerides (content >60%, by weight), therefore, also requires enrichment through distillation or crystallization. Accordingly, this process also is not a cost-effective alternative to the chemical process.

Published PCT Applications WO 90/13656 and WO 90/04033 (both Enzytech, Inc.) and U.S. Pat. Nos. 5,935,828 and 5,316,927 (both Zaks et al.) describe the production of monoglycerides by enzymatic alcoholysis with various alcohols and a little water in the mixture. Lipases are used in powder form or immobilized. In the Examples, the alcohol component is present in a 20-fold excess, and lipases are used in quantities of ca. 20% by weight, based on the triglyceride used.

Published PCT Applications WO 91/16441, and WO 91/16442 (both Procter and Gamble Company), and U.S. Pat. No. 5,116,745 (Mazur et al.) describe processes in which a mixed regioselective alcoholysis and hydrolysis of triglycerides to 1,2-diglycerides and 2-monoglycerides using lipases is carried out in the presence of a solvent, an alcohol and an aqueous buffer.

Published European Patent Application EP 0 407 959A2 (Lion Corporation) describes a process for the production of polyol fatty acid monoesters using an immobilized thermostable lipase in the presence of secondary or tertiary alcohols as solubilizers and reactants.

Published PCT Application WO 02/06505A1 (Nippon Suisan Kaisha Ltd.) describes regioselective alcoholysis using immobilized lipase, a large excess of alcohol and high concentration of enzyme, followed by re-esterification of the monoglyceride.

JP 03108489 and JP03187385 (Meito Sangyo Co. Ltd.) describe the regioselective hydrolysis of triglycerides with alkaline lipase in the presence of alkaline salts. The lipase used in only active under alkaline conditions.

JP 03103499 (Meito Sangyo Co. Ltd.) describes the regioselective alcoholysis of PUFA triglycerides with isobutanol in the presence of an alkaline lipase.

In the various enzymatic productions of partial glycerides that have been described in the above-cited documents, solvents are required, the water of reaction has to be removed at great expense and/or the lipases used are either very special (expensive) or immobilized. The low reaction rates compared with the conventional chemical synthesis, the long reaction times and hence high equipment utilization levels, and/or the high concentrations of alcohol to be reacted or high amounts of lipase needed, in order to achieve an acceptable yield of monoglycerides limit the utility of these processes. Even the use of inexpensive lipases leads to processes that make an industrial process impractical on cost grounds alone.

Now, the objective of the present invention was to provide an inexpensive variant to the known enzymatic production methods, in order to increase the yield of monoglycerides from polyol esters, such as triglycerides, for example, in enzymatic alcoholyses, and to keep the enzyme content to a minimum.

DETAILED DESCRIPTION OF THE INVENTION

The present invention relates to a process for the production of monoglycerides in which triglycerides are enzymatically reacted with an esterase that has been activated by addition of alkaline salts, in the presence of linear or branched alcohols containing 1 to 8 carbon atoms.

It has surprisingly been found that the addition of alkaline salts can activate esterases in order that, compared with known processes, an increased yield of monoglycerides may be achieved in the alcoholysis of monoglycerides.

In the process according to the invention, a triglycerides is split into a 2-monoglyceride and two fatty acid esters in the presence of an alcohol. The reaction may be carried out very economically through the use of small quantities of esterase, preferably lipase, in the presence of an added alkaline inorganic salt, which strongly activates the enzyme, such that a high conversion is achieved with a small quantity of enzyme concentrate, even without stabilization of the enzyme by immobilization. There is no need for the inclusion of additional solvents.

The alcoholysis is carried out at temperatures of 10° C. to 40° C., preferably at 10° C. to 30° C., and more particularly at a temperature of 15° C. to 25° C., with a water content including the water content of the liquid enzyme preparation of 0.1 to 10%, by weight, preferably 0.1 to 5%, by weight, and more particularly 0.1 to 2%, by weight, based on the weight of triglyceride. Although the reaction may be carried out with higher water contents, the content of free fatty acid formed is increased in that case. Such free fatty acid is undesirable, because it is capable of entering into a re-esterification in the separation of ester and glyceride mixture by distillation, thus reducing the yield of monoglyceride.

The reaction time is preferably 12 to 48 hours, depending on the enzyme concentration used. In a preferred embodiment, all the reactants are mixed and the reaction is initiated by the addition of the enzyme preparation.

The alcohol component containing 1 to 8 carbon atoms, preferably methanol and/or ethanol, preferably ethanol, is added either completely at the beginning of the reaction or over the duration of the reaction. The quantity of alcohol used is variable, between a minimum of 2 mols alcohol to 1 mol oil, and a maximum of 50%, by weight, alcohol and 50%, by weight, oil in the mixture.

In another step of the process according to the invention, the esterase may be deactivated by heat and the precipitated esterase may, optionally then be filtered off, in which case, not only the precipitated esterase, but also additives or formulation ingredients of the enzyme preparation used may be removed. At the same time, the alcohol component may be removed by distillation, for example, at 80° C./100 mbar vacuum, and a mixture of alkyl ester and monoglyceride is obtained, which mixture may be separated by distillation, for example, in a thin-layer evaporator or in a column. The reaction conditions are, for example, 175° C. and 0.3 mbar vacuum, with the monoglyceride remaining in the bottom product.

The esterases to be used in the enzymatic processes according to the invention are preferably those which are derived from an organism selected from the group consisting of *Thermomyces lanugenosus, Candida antarctica A, Candida antarctica B, Rhizomucor miehei, Candida cylindracea, Rhizopus javanicus, Porcine pancreas, Aspergillus niger, Candida rugosa, Mucor javanicus, Pseudomonas fluorescens, Rhizopus oryzae, Pseudompnas* sp., *Chromobacterium viscosum, Fusarium oxysporum* and *Penicilium camemberti*. Esterases from *Thermomyces lanugenosus*, also called *Humicola lanuginosa*, are particularly preferred.

Esterases are enzymes which catalyze the formation and hydrolysis of esters; as hydrolases, they split their respective substrates with the incorporation of the elements of water. The esterases include, for example, the fat-splitting lipases, which represent preferred esterases for the process according to the invention. The use of 1,3-regiospecific lipases is particularly preferred for the process according to the invention, these lipases being distinguished by the fact that they preferentially split off the fatty acids at the 1- and 3-positions of triglycerides. In principle, any 1,3-regioselective lipase or esterase, in free or immobilized form, may be used for the process according to the invention. The lipase of *Thermomyces lanugenosus*: Lipozyme® TL 100 1 or Lipolase® 100 EX (manufactured by Novozymes) has proven to be particularly preferred for the process according to the invention.

Experimental data have shown that the addition of small quantities of alkaline inorganic salts greatly increases the enzyme activity of the esterases used in the process according to the invention. In particular, non-immobilized lipases are activated by the alkaline salts.

The commercially-obtainable liquid lipase preparation is preferably used in a concentration of from 0.05 to 2%, based on the quantity of triglyceride used. These commercially-obtainable liquid enzyme preparations have an enzyme activity of, on average, 100,000 U/ml (one enzyme unit U being defined as the quantity of enzyme which catalyzes the reaction of one micromol of substrate per minute). In the process according to the invention, alkaline inorganic salts selected from the group consisting of hydroxides, carbonates and phosphates of sodium, potassium, calcium, magnesium and ammonium, predissolved in water, are preferably used to activate the esterase. According to the invention, the quantity of alkaline inorganic salts for activating the esterase is between 0.00001 and 1%, by weight, and preferably, between 0.0001 and 0.2%, by weight, based on the weight of triglyceride used. The quantity of alkaline salts used depends on the quantity of buffered liquid enzyme preparation used and on the strength of the base. Where NaOH and <0.5% liquid enzyme preparation are used, the concentration is in the lower range; where $Na_2CO_3$ and 2% liquid enzyme preparation are used, the quantity of alkaline salts is in the upper concentration range.

Surprisingly, the strongest activation of the *Thermomyces lanugenosus* lipase was achieved when salts such as, for example, trisodium phosphate, sodium carbonate, sodium hydroxide or ammonium hydroxide, were added to the commercially-obtainable liquid enzyme preparation in quantities of 0.0001 to 0.2% by weight (based on the triglyceride content). Surprisingly, a faster monoglyceride synthesis rate was thus achieved than with *Thermomyces* lipase absorbed onto polypropylene. the activation of the lipase is so strong that it cannot be explained by the pH shift in the reaction medium alone. If the *Thermomyces lanugenosus* lipase is used in immobilized form under the same conditions, there is not sign of equally strong activation by the addition of alkaline salts. This strong activation is very surprising, as it is generally accepted that a high activity level can only be achieved in the low-water medium with lipases fixed to a carrier. The strong activation eliminates the need for elaborate immobilization processes and leads to a simplified production installation. In addition, measurement of the pH value of the reacted product mixture shows that the pH is in the neutral-to-mildly acidic range, which makes enzyme activation by pH shift alone improbable.

Triglycerides from fats and oils which have a high percentage content of mono- and/or polyunsaturated fatty acids, and which are selected from the group consisting of sunflower oil, rapeseed oil, thistle oil, soybean oil, linseed oil, peanut oil, tallows, olive oil, castor oil, palm oil, and old oils, for example, used frying fat, are preferably used in the process according to the invention.

Peanut oil, with a melting point of 2 to 3° C., contains on average, based on fatty acid, 54% by weight oleic acid, 24% by weight linoleic acid, 1% by weight linolenic acid, 1% by weight arachic acid, 10% by weight palmitic acid and 4% by weight stearic acid.

Linseed oil typically contains 5% by weight palmitic acid, 4% by weight stearic acid, 22% by weight oleic acid, 17% by weight linoleic acid and 52% by weight linolenic acid. It has an iodine value of 155 to 205, a saponification value of 188 to 196, and a melting point of ca. −20° C.

Olive oil mainly contains oleic acid. Palm oil contains ca. 2% by weight myristic acid, 42% by weight palmitic acid, 5% by weight stearic acid, 41% by weight oleic acid, and 10% by weight linoleic acid as fatty acid components.

Rapeseed oil typically contains ca. 48% by weight erucic acid, 15% by weight oleic acid, 14% by weight linoleic acid, 8% by weight linolenic acid, 5% by weight eicosenoic acid, 3% by weight palmitic acid, 2% by weight hexadecenoic acid and 1% by weight docosadienoic acid as fatty acid components. Rapeseed oil from new plants has highter levels of the unsaturated acids. Typical fatty acid levels in rapeseed oil are erucic acid: 0.5% by weight, oleic acid: 63% by weight, linoleic acid: 20% by weight, linolenic acid: 9% by weight, eicosenoic acid: 1% by weight, palmitic acid: 4% by weight, hexadecenoic acid: 2% by weight and docosadienoic acid: 1% by weight.

80 to 85% by weight of castor oil consists of the glyceride of ricinoleic acid, with the remainder including ca. 7% by weight oleic acid glycerides, 3% by weight linoleic acid glycerides and ca. 2% by weight palmitic and stearic acid glycerides.

Soybean oil contains 55 to 65% by weight, based on total fatty acids, of polyunsaturated acids, more particularly, linoleic and linolenic acid. The situation is similar with sunflower oil, of which the typical fatty acid spectrum, based on total fatty acids, is: ca. 1% by weight myristic acid, 3 to 10% by weight palmitic acid, 14 to 65% by weight oleic acid and 20 to 75% by weight linoleic acid.

All of the above-mentioned figures relating to the percentage fatty acid contents in the triglycerides are known to depend on the raw materials used and can vary accordingly.

The fatty acid composition in each mixture is made up of the particular native fatty acid composition of the vegetable oil used and the particular quality of the raw material from which the methyl and/or ethyl esters and the monoglycerides, are produced, in a known manner.

Linear or branched alcohols containing 1 to 8 carbon atoms are preferably used as alcohol components for the process according to the invention. these alcohols are preferably primary or secondary alcohols, ethanol or 1-propanol being the preferred alcohol component. The alcohol content is preferably 10 to 75% by weight, based on the triglyceride used, 15 to 40% by weight more preferably being used. The monoglyceride content is dependent upon the quantity of alcohol used.

In a preferred embodiment of the process according to the invention, the alcohol may be removed, preferably by distillation. Through this additional process step, monoglycerides are obtained in admixture with alkyl esters which may be used in the form of the mixture as a lubricant additive, as an additive for plastics, or as an emulsifying constituent in foods, cosmetic and/or pharmaceutical formulations. Accordingly, the present invention also relates to the use of monoglycerides in admixture with the alkyl esters present in the reaction mixture as a lubricant additive, as an additive for fuels or as an emulsifying constituent in foods, cosmetic and/or pharmaceutical formulations.

In another preferred embodiment of the process according to the invention, the alkyl esters may be removed from the monoglycerides, preferably by distillation. Through this additional process step, monoglycerides are obtained which may be used as a lubricant additive, as an additive for fuels, or as an emulsifying constituent in foods, cosmetic and/or pharmaceutical formulations. Accordingly, the present invention also relates to the use of monoglycerides produced by the process according to the invention, after removal of the alcohol and the alkyl esters, as an emulsifying constituent in foods, cosmetic and/or pharmaceutical formulations.

The present invention also relates to the use of monoglycerides produced by the process according to the invention in admixture with alcohol and alkyl esters as a lubricant additive or as an additive for fuels.

The use of various additives for fuels is known from the literature. Monoglycerides and other partially-esterified or -etherified polyols (for example, even glycol monoesters) are added as a diesel additive because they have a good lubricating effect. Patent applications which describe such additives include, for example published applications EP 0 721 492 (Infineum USA L.P.). WO 01/19941 (Fina Research S.A.) and WO 00/63322 (Pure Fuels USA Inc.). More particularly, glyceride mixtures with a high percentage of monoglyceride demonstrate good lubricating properties. Thus, it has been found that the monoglycerides produced by the process according to the invention may also be used as fuel additives in diesel fuel with good lubricating properties.

The regiospecific fatty acid composition of the naturally-occurring oils may be utilized in the process according to the invention. The monoglyceride fraction mainly contains the fatty acid composition which is to be found in the 2-position of the oils. With most naturally-occurring oils, the more highly unsaturated fatty acids are preferably bound in the 2-position. In this way, monoglycerides with a high linoleic acid content may be produced, for example, from sunflower or thistle oil. These monoglycerides have a reduced solidification point which is particularly important for the use of monoglycerides as a diesel additive. A monoglyceride with a high oleic acid content may be obtained, for example, from palm oil. This monoglyceride is particularly suitable for use in foods or cosmetic products.

The use of monoglycerides in foods is known from the literature. Under [[EU]] European Union guidelines, the content of mono- and diglyceride must be at least 70%, the acid value should not exceed 6, and the product should contain at most 7% free glycerol and 2% water. Monoglycerides with a mono- and diester content of >90% and a monoester content of >70% are obtained by the enzymatic process coupled with removal of the fatty acid esters by distillation. The water content, the free glycerol content and the acid value are well below the maximum values. Accordingly, monoglycerides produced by the process according to the invention satisfy the criteria for use in foods.

The use of monoglycerides in cosmetic or pharmaceutical formulations is also known from the literature. The monoglycerides produced in accordance with the invention with a mono- and diester content of >90%, and a monoester content of >70%, may be used as water-in-oil emulsifiers, co-emulsifiers, lipid layer enhancing components of consistency factors in creams, lotions, ointments, surfactant preparations and in cosmetic and pharmaceutical water-in-oil (w/o) and oil-in-water (o/w) emulsions.

EXAMPLES

Example 1

Regioselective Alcoholysis with Various Enzymes in Free and Immobilized Form

Sixteen mixtures consisting of 20 g rapeseed oil and 2.5 g ethanol were placed in glass beakers equipped with magnetic stirrers. 0.25 g water was added, with stirring, to mixtures 1 to 9, 15 and 16; 0.5 g water was added to mixtures 10 to 14. Lipases in free and immobilized form as listed in the following Table were then added. The mixtures were incubated with stirring for 24 hours, another 2.5 g ethanol being added after 5 hours. The alcoholysis of mixtures 1 to 14 was carried out at room temperature on a multistirrer plate. Mixtures 15 and 16 were incubated at 45° C. on a shaker. After 24 hours, samples were taken and the content of glycerides and ethyl esters was analyzed by gas chromatography. The results were reported as percentage areas. Small amounts of fatty acid formed are contained in the ethyl ester area.

The immobilizates of mixtures 1 to 3, 15 and 16 were acquired in immobilized form direct from the manufacturer. The immobilizates of mixtures 4 to 8 were prepared by adsorption onto Accurel® MP 1000 (Membrana). To this end, Accurel® MP 1000 was incubated for 1 hour in 10 ml ethanol. After the ethanol had been decanted off, 10 g water and 0.5 g of each lipase preparation were added. The mixture was incubated overnight at room temperature. The immobilizate was then separated by filtration and dried for 24 hours at room temperature on sheets of paper.

carried out at room temperature on a multistirrer plate. Samples were taken after 16 hours and 44 hours and the content of glycerides was analyzed by gas chromatography. The results were reported as percentage areas.

| Mixture | Duration | % Ethyl ester | Monoglyceride content | Mono-:di-:triglyceride ratio |
|---|---|---|---|---|
| 1 | 16 | 0 | 0% | 0:12:88 |
| 1 | 44 | 0.7 | 0% | 0:4:96 |
| 2 | 16 | 55.1 | 26.5% | 63:33:4 |
| 2 | 44 | 61.1 | 23.3% | 69:31:0 |
| 3 | 16 | 0.7 | 0% | 0:2:98 |
| 3 | 44 | 2.2 | 0% | 0:4:96 |
| 4 | 16 | 0.7 | 0% | 0:2:98 |
| 4 | 44 | 2.2 | 0% | 0:4:96 |

| Mixture | Enzyme | Manufacturer | Organism | Form |
|---|---|---|---|---|
| 1 | 1 g Novozym 435 | Novozymes | C. antarctica B | Immobilizate |
| 2 | 1 g Lipozym RM IM | Novozymes | R. miehei | Immobilizate |
| 3 | 1 g Lipozym TL IM | Novozymes | T. lanugenosus | Immobilizate |
| 4 | 1 g Lipase FAP 15/MP 1000 | Amano | R. oryzae | Immobilizate |
| 5 | 1 g Lipase A/MP 1000 | Amano | A. niger | Immobilizate |
| 6 | 1 g Lipase M/MP 1000 | Amano | M. javanicus | Immobilizate |
| 7 | 1 g Lipase L115/MP 1000 | Biocatalysts | Porcine pancreas | Immobilizate |
| 8 | 1 g Lipomod 36/MP 1000 | Biocatalysts | R. javanicus | Immobilizate |
| 9 | 0.5 g Lipolase | Novozymes | T. lanugenosus | Free |
| 10 | 0.5 g Lipase FAP 15/MP 1000 | Amano | R. oryzae | Free |
| 11 | 0.5 g Lipase A/MP 1000 | Amano | A. niger | |
| 12 | 0.5 g Lipase M/MP 1000 | Amano | M. javanicus | |
| 13 | 0.5 g Lipase L115/MP 1000 | Biocatalysts | Porcine pancreas | |
| 14 | 0.5 g Lipomod 36/MP 1000 | Biocatalysts | R. javanicus | |
| 15 | 1 g Novozym 435 | Novozymes | C. antarctica B | Immobilizate |
| 16 | 1 g Lipozym RM IM | Novozymes | R. miehei | Immobilizate |

| Mixture | % Ethyl ester | % Monoglyceride | % Diglyceride | % Triglyceride |
|---|---|---|---|---|
| 1 | 18.2 | 1.4 | 5.0 | 75.4 |
| 2 | 39.3 | 16.2 | 14.5 | 29.5 |
| 3 | 62.7 | 23.5 | 10.9 | 0.5 |
| 4 | 58.5 | 29.6 | 9.6 | 0.0 |
| 5 | 5.2 | 1.6 | 4.6 | 88.6 |
| 6 | 41.7 | 16.5 | 27.7 | 14.1 |
| 7 | 82.4 | 6.8 | 7.0 | 2.9 |
| 8 | 57.7 | 32.7 | 8.3 | 0.0 |
| 9 | 15.9 | 4.1 | 14.8 | 65.2 |
| 10 | 0.0 | 0.0 | 2.1 | 96.2 |
| 11 | 2.0 | 0.4 | 1.6 | 96.0 |
| 12 | 3.4 | 0.0 | 2.4 | 94.2 |
| 13 | 2.2 | 0.4 | 2.3 | 95.1 |
| 14 | 3.3 | 0.0 | 2.8 | 93.9 |
| 15 | 41.0 | 0.0 | 2.2 | 55.8 |
| 16 | 3.7 | 0.0 | 2.3 | 94.0 |

Example 2

Regioselective Alcoholysis of Sunflower Oil with Non-immobilized Lipases

Six mixtures consisting of 40 g sunflower oil and 10 g ethanol were placed in glass beakers equipped with magnetic stirrers. 0.4 g water was added with stirring. 40 mg solid $Na_3PO_4 \times 12\ H_2O$ were added to mixtures 2, 4 and 6. 0.4 g lipolase (*Thermomyces lanugenosus* lipase, liquid preparation) was added to mixtures 1 and 2, 0.4 g Novozym® 525 (*Candida antarctica B* lipase, liquid preparation) to mixtures 3 and 4 and 0.4 g Novozym® 388 (*Rhizomucor miehei* lipase, liquid preparation) to mixtures 5 and 6. The alcoholysis was -continued

| Mixture | Duration | % Ethyl ester | Monoglyceride content | Mono-:di-:triglyceride ratio |
|---|---|---|---|---|
| 5 | 16 | 7.6 | 0% | 0:4:96 |
| 5 | 44 | 4.9 | 1.2% | 2:7:91 |
| 6 | 16 | 2.1 | 0% | 0:3:97 |
| 6 | 44 | 4.1 | 0.9% | 1:5:94 |

Result:

Lipolase® lipase in the presence of a basic salt showed significant activity (mixture 2). If, by contrast, no salt was added, only a very weak alcoholysis reaction could be detected. Weak activity was detected with Novozym® 388, but was not dependent on the addition of salt.

Example 3

Comparison of the Activity of Immobilized Lipolase® Lipase and Lipolase Liquid Preparation Mixtures containing 0.2 g Lipolase liquid preparation or a corresponding amount of Lipolase fixed to a carrier were compared.

Immobilization of Lipolase® lipase on Accurel® MP 1000 (Membrana): 5 g MP 1000 were placed in a 250 ml Erienmeyer flask and 15 ml ethanol was added. The mixture was shaken for 1 hour, after which ethanol was decanted off. 50 g water was added to the Accurel® MP 1000 support. After stirring for 1 hour, the water was decanted off. 100 ml phosphate buffer, 20 mM, pH 6.0, was added and the immobilization was started by addition of 5 g Lipolase liquid preparation. The mixtures were stirred overnight at 8° C., after which the enzyme immobilizate was filtered off. The immobilizate was dried overnight at room temperature between paper towels. The immobilizate was weighed out and a quantity of immobilize corresponding to 0.2 g Lipolase liquid preparation was used for the alcoholysis.

Immobilization of Lipolase® lipase on Accurel® MP 1000 (Membrana), alternative: Immobilization was carried out as described above. After the immobilizate had been filtered off, 5 ml of a 200 mM $Na_3PO_4$ solution were added. The complete mixture was dried in vacuo at room temperature. The object of this additional step was to prepare an already alkaline immobilizate. The immobilizate was weighed out and a quantity of immobilizate corresponding to 0.2 g lipolase liquid preparation was used for the alcoholysis.

Immobilization of Lipolase on Dowex® Marathon WBA (Dow Chemical): 200 mg Dowex® WBA (weak base anion exchange resin) were placed in a small glass beaker. 0.2 g Lipolase liquid preparation were added by pipette and thoroughly mixed with the tip of a pipette. The mixture was incubated for 2 hours at room temperature with occasional mixing. The complete mixture (Dowex® resin+supernatant) was used for the transformation. Parallel tests where unbound Lipolase was obtained from the immobilizate by washing out showed that around 90% of the Lipolase present was fixed to a carrier.

Immobilization of Lipolase on Duolite® A 568 (Rohm & Haas): 200 mg Duolite® A 568 anion resin were placed in a small glass beaker. 0.2 g Lipolase liquid preparation were added by pipette and thoroughly mixed with the tip of a pipette. The mixture was incubated for 2 hours at room temperature with occasional mixing. The complete mixture (resin+supernatant) was used for the transformation. Parallel tests where unbound Lipolase was obtained from the immobilizate by washing out showed that around 80% of the lipase present was fixed to a carrier.

Test Procedure:

Ten mixtures consisting of 40 g sunflower oil and 10 g ethanol were placed in glass beakers equipped with magnetic stirrers. 0.4 g water was added, with stirring. 50 mg solid $Na_2CO_3$ were added to mixtures 2, 4, 6, 8 and 10. 0.2 g Lipolase (*Thermomyces lanugenosus* lipase, liquid preparation) was added to mixtures 1 and 2, the Dowex® resin immobilizates to mixtures 3 and 4, the Duolite® resin immobilizates to mixtures 5 and 6, the MP 1000 support immobilizates to mixtures 7 and 8 and the MP 1000 support immobilizates after treated with $Na_3PO_4$ to mixtures 9 and 10. The alcoholysis was carried out at room temperature on a multi-stirrer plate. Mixtures 3 to 10 were treated twice. Samples were taken after 16 hours and the content of glycerides was analyzed by gas chromatography. The results were reported as percentages areas.

| Mixture | % Ethyl ester | Monoglyceride content | Mono-:di-:triglyceride ratio |
|---|---|---|---|
| 1 | 0 | 0% | 0:3:97 |
| 2 | 56.1 | 28.5% | 70:30:0 |
| 3 (1) | 25.6 | 11.5% | 16:23:61 |
| 3 (2) | 26.4 | 10.2% | 14:18:68 |
| 4 (1) | 31.6 | 14.1% | 21:36:44 |
| 4 (2) | 37.9 | 15.7% | 26:30:45 |
| 5 (1) | 17.6 | 7.4% | 9:13:78 |
| 5 (2) | 22.6 | 9.3% | 12:15:73 |
| 6 (1) | 35.5 | 17.1% | 27:34:39 |
| 6 (2) | 28.5 | 12.8% | 18:19:63 |
| 7 (1) | 15.5 | 5.5% | 7:20:73 |
| 7 (2) | 24.8 | 8.5% | 11:27:61 |
| 8 (1) | 26.1 | 10.5% | 14:37:49 |
| 8 (2) | 44.1 | 20.0% | 36:40:24 |
| 9 (1) | 24.4 | 9.1% | 12:43:45 |
| 9 (2) | 14.2 | 3.5% | 4:13:83 |
| 10 (1) | 8.4 | 2.4% | 3:18:79 |
| 10 (2) | 15.9 | 4.3% | 5:14:81 |

Result:

All the immobilizates containing lipase showed alcoholysis activity. With the exception of the immobilizate pretreated with $Na_3PO_4$, all the immobilizates showed additional activation by $Na_2CO_3$. However, the activation of the liquid lipase by $Na_2CO_3$ is considerably stronger than the activation of the immobilizates. For the same weighed quantity of enzyme, alcoholysis with salt-activated Lipolase lipase (mixture 2) was much faster than with the immobilizates.

Example 4

Reaction with Various Alcohols

Various mixtures consisting of 40 g sunflower oil and variable quantities of various alcohols were subjected to an alcoholysis reaction with Lipolase lipase at room temperature. The mixtures had the composition shown in the following Table:

| Mixture | Alcohol | Water | Salt | Lipolase |
|---|---|---|---|---|
| 1 | 10 g Ethanol | 0.4 g | 40 mg $Na_3PO_4$ | 0.4 g |
| 2 | 13 g Propanol | 0.4 g | 40 mg $Na_3PO_4$ | 0.4 g |
| 3 | 13 g Isopropanol | 0 g | 40 mg $Na_3PO_4$ | 1.2 g |
| 4 | 16 g Butanol | 0.4 g | 40 mg $Na_3PO_4$ | 0.4 g |
| 5 | 16 g Isobutanol | 0 g | 40 mg $Na_3PO_4$ | 1.2 g |
| 6 | 19 g Isoamyl alcohol | 0.4 g | 40 mg $Na_3PO_4$ | 0.8 g |
| 7 | 22 g Hexanol | 0.4 g | 40 mg $Na_3PO_4$ | 0.4 g |
| 8 | 28 g 2-Ethylhexanol | 0.4 g | 40 mg $Na_3PO_4$ | 1.2 g |
| 9 | 7 g Methanol | 0 g | 40 mg $Na_3PO_4$ | 1.2 g |
| 10 | 16 g Butanol | 0 g | 25 mg $Na_2CO_3$ | 1.2 g |
| 11 | 16 g Butanol | 0 g | 50 mg $Na_2CO_3$ | 0.6 g |
| 12 | 16 g Butanol | 0.8 g | 50 mg $Na_2CO_3$ | 0.6 g |
| 13 | 23 g Hexanol | 0.8 g | 25 mg $Na_2CO_3$ | 1.2 g |
| 14 | 24 g Hexanol | 2.8 g | 25 mg $Na_2CO_3$ | 1.2 g |
| 15 | 22 g Hexanol | 2.8 g | 50 mg $Na_2CO_3$ | 0.6 g |

The content of glycerides and esters was analyzed by gas chromatography. The results were evaluated as percentage areas, the excess free alcohols not being included. Samples were taken at the times shown in the Table.

| Mixture | Duration [h] | % Alkyl ester | Monoglyceride content | Mono-:di-:triglyceride ratio |
|---|---|---|---|---|
| 1 | 16 | 59.3 | 26.4% | 72:28:0 |
| 2 | 16 | 58.8 | 28.3% | 74:26:0 |
| 3 | 16 | 30.6 | 8.7% | 13:55:32 |
| 4 | 44 | 42.1 | 17.1% | 30:44:26 |
| 5 | 44 | 41.4 | 17.9% | 31:41:28 |
| 6 | 44 | 43.5 | 17.1% | 31:46:23 |
| 7 | 44 | 25.1 | 6.9% | 9:36:55 |
| 8 | 44 | 27.8 | 14.5% | 37:42:20 |
| 9 | 16 | 43.7 | 18.3% | 34:12:54 |
| 10 | 40 | 59.7 | 26.3% | 70:30:0 |
| 11 | 16 | 57.9 | 26.5% | 67:29:4 |
| 12 | 16 | 29.4 | 11.9% | 17:33:50 |
| 13 | 40 | 29.3 | 9.2% | 13:43:44 |
| 14 | 40 | 69.9 | 19.6% | 67:33:0 |
| 15 | 16 | 29.6 | 18.0% | 26:45:30 |

Result:

An alcoholysis reaction was observed with all the alcohols used. The enzyme catalyzes the reaction with primary and secondary alcohols and linear and branched alcohols. The best reaction was observed with the alcohols ethanol and propanol in a reaction medium containing 2% water. For the other alcohols, the reaction conditions had to be slightly modified in part in order to achieve an optimal conversion. Detailed investigations with butanol (mixtures 10 to 12) and with hexanol (mixtures 13 to 15) showed that, even with these alcohols, the production of glycerides with a monoglyceride content of >60% is possible. The reaction with butanol takes place better in the medium containing relatively little water, whereas the reaction with hexanol only takes place successfully in the presence of relatively large quantities of water. It may generally be concluded from this that the concentration of water has to be increased if the alcohol becomes more hydrophobic in order to achieve an optimal reaction rate.

Example 5

Influence of Ethanol Concentration on Glycerol Formation, Acid Formation and Monoglyceride Content Various mixtures consisting of 40 g sunflower oil and variable quantities of ethanol were subjected to an alcoholysis reaction with 0.2 g Lipolase® lipase at room temperature. Quantities of 25 mg Na$_2$CO$_3$ were added. The mixtures had the composition shown in the following Table:

| Mixture | Ethanol | Water |
|---|---|---|
| 1 | 15 g | 0.2 g |
| 2 | 30 g | 0.2 g |
| 3 | 15 g | 0.4 g |
| 4 | 30 g | 0.4 g |
| 5 | 15 g | 0.8 g |
| 6 | 30 g | 0.8 g |

The content of glycerides was analyzed by gas chromatography. The results were expressed as percentage areas. The glycerol content was also analyzed by gas chromatography. The results are expressed as non-calibrated percentage areas. According to mass balance, the absolute glycerol contents are lower, although the key factor here is comparison of the relative values. GC samples were taken after a reaction time of 16 hours for the glycerol determination and after a reaction time of 40 hours for the glyceride determination. Acid values were determined after 16 hours.

| Mixture | Acid value | % Glycerol | % Ethyl ester | % Monoglyceride | Mono-:di-:triglyceride ratio |
|---|---|---|---|---|---|
| 1 | 2 | 1.5% | 62.2 | 29.2% | 86:14:0 |
| 2 | 1 | 0.3% | 34.5 | 11.4% | 18:35:47 |
| 3 | 3 | 2.4% | 64.3 | 26.2% | 86:14:0 |
| 4 | 1 | 0.5% | 58.9 | 30.6% | 77:23:0 |
| 5 | 5 | 2.8% | 64.7 | 25.8% | 87:13:0 |
| 6 | 2 | 1.1% | 62.4 | 32.2% | 92:8:0 |

Since glycerol shows a comparatively stronger adsorption than the ethyl esters and glycerides in the GC method used, a calibration was carried out directly in a mixture of ethyl ester, free ethanol and glycerides. The adsorption over a concentration range of 0 to 1.0% by weight glycerol corresponds to the formula:

$$y=2.3x (y=\text{adsorption}, x=\text{weighed amount})$$

The following pattern emerges from the above analysis:

| Mixture | Glycerol measured | Glycerol (% by wt.) after calibration |
|---|---|---|
| 1 | 1.5 | 0.65 |
| 2 | 0.3 | 0.13 |
| 3 | 2.4 | 1.04 |
| 4 | 0.5 | 0.22 |
| 5 | 2.8 | 1.22 |
| 6 | 1.1 | 0.48 |

Result:

The higher the concentration of alcohol used, the higher the monoglyceride contents obtained. Based on the total glycerides, monoglyceride contents of more than 90% can be achieved.

An increase in the alcohol content led to a reduction in the formation of by-products, such as free fatty acid or glycerol formed from the total hydrolysis of the oil.

The reaction rate was reduced when the alcohol content was increased. The reaction rate was improved by increasing the water content, in order that good monoglyceride formation was achieved, even with a large molar excess of ethanol (mixture 6).

Example 6

Reaction with Various Oils

Hydrolysis was investigated in parallel tests using various oils. Quantities of 40 g of the oil were weighed into glass beakers with 10 g ethanol. Quantities of 0.4 g water were added with stirring, followed by the addition of 40 mg solid Na$_3$PO$_4$×12 H$_2$O. The reaction was started by the addition of 0.4 g Lipolase lipase. After a reaction time of 16 hours, a sample was taken for analysis by gas chromatography. The results are expressed as percentages areas.

| Mixture | Oil | % Ethyl ester | % Monoglyceride | Mono-:di-:triglyceride ratio |
|---|---|---|---|---|
| 1 | Sunflower oil | 59.3 | 26.4% | 72:28:0 |
| 2 | Rapeseed oil | 58.7 | 26.4% | 73:27:0 |

-continued

| Mixture | Oil | % Ethyl ester | % Monoglyceride | Mono-:di-:triglyceride ratio |
|---|---|---|---|---|
| 3 | Thistle oil | 60.9 | 26.0% | 76:24:0 |
| 4 | Sunflower oil 2 | 60.0 | 26.7% | 76:24:0 |
| 5 | Castor oil | 57.5 | 30.0% | 73:27:0 |
| 6 | Soybean oil | 60.3 | 26.4% | 75:25:0 |
| 7 | Fish oil | 51.0 | 35.0% | 78:22:0 |
| 8 | 50% rapeseed oil + 50% palm oil | 60.7 | 25.9% | 75:25:0 |
| 9 | Lard | 75.4 | 20.7% | 72:28:0 |

Result:
Good alcoholysis was observed with all the oils used. A monoglyceride content of >70%, based on total glycerides, was achieved with all the oils.

Example 7

Reaction with Various Alkaline Salts

Five mixtures of 40 g sunflower oil and 10 g ethanol were weighed in. 0.4 g water was added, with stirring, to all 5 mixtures. 40 mg $Na_3PO_4 \times 12\ H_2O$ was added to mixture 1; 11 mg $Na_2CO_3$ to mixture 2; 4 mg $Ca(OH)_2$ to mixture 3; and 31 mg trisodium citrate$\times 2\ H_2O$ to mixture 4. No salt was added to mixture 5. The reactions were started by the addition of 0.4 g Lipolase. After a reaction time of 16 hours, a sample was taken for analysis by gas chromatography. The results are expressed as percentage areas.

| Mixture | % Ethyl ester | Monoglyceride content | Mono-:di-:triglyceride ratio |
|---|---|---|---|
| 1 | 59.3 | 26.4% | 72:28:0 |
| 2 | 62.1 | 23.3% | 74:26:0 |
| 3 | 50.5 | 28.9% | 65:35:0 |
| 4 | 1.0 | 0% | 0:3:97 |
| 5 | 0.7 | 0% | 0:2:98 |

Result:
The alcoholysis reaction was successful with the additions of phosphate salts, carbonate salts and hydroxides.

Example 8

Optimization of the Salt Concentration Used (for $Na_2CO_3$)

Twelve mixtures of 40 g sunflower oil and 10 g ethanol were weighed in. 0.2 g water was added, with stirring, to mixtures 1 to 6, and 0.4 g water to mixtures 7 to 12. Various quantities of salt, as shown in the following Table, were then added. The reactions were started by the addition of 0.2 g Lipolase lipase. After a reaction time of 16 hours, a sample was taken for analysis by gas chromatography. The results are expressed as percentage areas.

| Mixture | $Na_2CO_3$ | % Ethyl ester | Monoglyceride content | Mono-:di-:triglyceride ratio |
|---|---|---|---|---|
| 1 | 10 mg | 30.0 | 14.7% | 21:32:47 |
| 2 | 25 mg | 53.0 | 29.3% | 65:32:3 |
| 3 | 50 mg | 54.5 | 30.2% | 70:30:0 |
| 4 | 100 mg | 55.9 | 29.1% | 70:30:0 |
| 5 | 200 mg | 43.4 | 22.4% | 41:41:19 |
| 6 | 500 mg | 4.4 | 0.9% | 1:7:92 |
| 7 | 10 mg | 44.2 | 23.5% | 43:38:19 |
| 8 | 25 mg | 50.3 | 27.2% | 56:38:6 |
| 9 | 50 mg | 55.4 | 30.2% | 72:28:0 |
| 10 | 100 mg | 56.9 | 28.5% | 72:28:0 |
| 11 | 200 mg | 57.2 | 27.5% | 70:30:0 |
| 12 | 500 mg | 36.1 | 16.4% | 26:39:35 |

Result
An increase in the water content in the mixture produces a slight shift in the optimal quantity of $Na_2CO_3$. With an addition of 0.2 g water, the range for the optimal quantity of salt extends from 25 mg to 100 mg, whereas, with an addition of 0.4 g water, the optimal range is between 50 mg and 200 mg.

It should be noted that the optimum basic additive depends on the quantity of buffered enzyme solution used and on the strength of the base. The test series with $Na_2CO_3$ may be regarded as exemplary.

Example 9

Influence of Temperature on the Transesterification Rate

Six mixtures of 40 g sunflower oil and 10 g ethanol were weighed in. 0.4 g water and 50 mg $Na_2CO_3$ were added to the mixtures with stirring. The reactions were started by the addition of 0.2 g Lipolase lipase. The reactions were carried out at different temperatures as shown in the following Table. After a reaction time of 24 hours, a sample was taken for analysis by gas chromatography. The results are expressed as percentage areas.

| Mixture | Temperature °C. | % Ethyl ester | Monoglyceride content | Mono-:di-:triglyceride ratio |
|---|---|---|---|---|
| 1 | 20° C. | 30.0 | 14.7% | 21:32 47 |
| 2 | 25° C. | 53.0 | 29.3% | 65:32:3 |
| 3 | 30° C. | 54.5 | 30.2% | 70:30:0 |
| 4 | 35 C. | 55.9 | 29.1% | 70:30:0 |
| 5 | 40° C. | 43.4 | 22.4% | 41:41:19 |
| 6 | 45° C. | 4.4 | 0.9% | 1:7:92 |

Result:
The Lipolase lipase is clearly deactivated even at temperatures as low as 30° C. The optimal reaction temperature is in the range from 20 to 25° C.

Example 10

Alcoholysis of Sunflower Oil and Enrichment of the Monoglyceride by Distillation 1.6 kg sunflower oil and 0.4 kg ethanol were weighed into a heatable, double-jacketed reactor. 16 g water and 0.44 g $Na_2CO_3$ were added, with stirring. The reaction was initiated by the addition of 8 g Lipolase and was carried out, with stirring, at room temperature. After 8 hours, another 0.8 kg ethanol was added to the mixture. After 40 hours, the reaction was terminated and a sample was analyzed by gas chromatography. The reaction mixture was heated, with stirring, to 80° C. Vacuum was applied and the excess ethanol was evaporated from the reaction mixture. The reaction mixture was then expanded to normal pressure and 16 g Tonsil and 6 g water were added. The mixture was stirred for 30 mins. at 80° C. and then for one hour in vacuo at 80° C. to remove residual water from the reaction mixture. After expansion of the reaction mixture to normal pressure, the mixture was filtered while warm. A sample was taken for analysis by gas chromatography. The mixture was then separated by short-path distillation. The reaction parameters were 180° C. and 0.5 mbar for a cooling finger temperature of 25° C. and a receiver temperature of 80° C. A mass balance of the distillation showed 29.8% by weight bottom product and 70.2% by weight distillate. The monoglyceride-containing bottom product was subjected to analysis by gas chromatography.

| Sample | % Ethyl ester | % Monoglyceride | % Diglyceride | % Triglyceride |
|---|---|---|---|---|
| After enz. reaction | 61.6 | 30.0 | 4.0 | 0 |
| After EtOH removal | 61.4 | 30.5 | 4.0 | 0 |
| After distillation | 3.3 | 81.2 | 14.9 | 0.7 |

| Sample | Ester/glycerides ratio | Mono-:di-:triglyceride ratio |
|---|---|---|
| After enz. reaction | 64:36 | 88:12:0 |
| After EtOH removal | 63:37 | 86:14:0 |
| After distillation | 3:97 | 84:15:1 |

Example 11

Alcoholysis of New Sunflower Oil and Enrichment of the Monoglyceride by Distillation 1.5 kg new sunflower oil and 0.75 kg ethanol were weighed into a heatable double-jacketed reactor. 15 g water and 1.5 g Na$_2$CO$_3$ were added with stirring. The reaction was initiated by addition of 7.5 g Lipolase and was carried out with stirring at room temperature. After 46 hours, the reaction was terminated and a sample was analyzed by gas chromatography. The reaction mixture was heated with stirring to 80° C. Vacuum was applied and the excess ethanol was evaporated from the reaction mixture. The reaction mixture was then expanded to normal pressure and 16 g Tonsil® fullers earth (Süd-Chemie) and 6 g water were added. The mixture was stirred for 30 mins. at 80° C. and then for one hour in vacuo at 80° C. in order to remove residual water from the reaction mixture. After expansion of the reaction mixture to normal pressure, the mixture was filtered while warm. A sample was taken for analysis by gas chromatography. The mixture was then separated by short-path distillation. the reaction parameters were 180° C. and 0.5 mbar for a cooling finger temperature of 25° C. and a receiver temperature of 80° C. The monoglyceride-containing bottom product was subjected to analysis by gas chromatography.

| Sample | % Ethyl ester | % Monoglyceride | % Diglyceride | % Triglyceride |
|---|---|---|---|---|
| After enz. reaction | 60.5 | 27.6 | 7.1 | 0 |
| After EtOH removal | 62.1 | 25.8 | 7.9 | 0 |
| After distillation | 8.0 | 72.0 | 20.0 | 0 |

| Sample | Ester/glycerides ratio | Mono-:di-:triglyceride ratio |
|---|---|---|
| After enz. reaction | 64:36 | 88:20:0 |
| After EtOH removal | 65:35 | 77:23:0 |
| After distillation | 8:92 | 78:22:0 |

Example 12

Alcoholysis of Thistle Oil and Enrichment of the Monoglyceride by Distillation 1.5 kg thistle oil and 0.75 kg ethanol were weighed into a heatable double-jacketed reactor. 15 g water and 1.5 g Na$_2$CO$_3$ were added with stirring. The reaction was initiated by the addition of 15 g Lipolase lipase and was carried out with stirring at room temperature. After 20 hours, the reaction was terminated and a sample was analyzed by gas chromatography. The reaction mixture was heated with stirring to 80° C. Vacuum was applied and the excess ethanol was evaporated from the reaction mixture. The reaction mixture was then expanded to normal pressure and 16 g Tonsil® and 6 g water were added. The mixture was stirred for 30 mins. at 80° C. and then for one hour in vacuo at 80° C. in order to remove residual water from the reaction mixture. After expansion of the reaction mixture to normal pressure, the mixture was filtered while warm. A sample was taken for analysis by gas chromatography. The mixture was then separated by short-path distillation. The reaction parameters were 180° C. and 0.5 mbar for a cooling finger temperature of 25° C. and a receiver temperature of 80° C. The monoglyceride-containing bottom product was subjected to analysis by gas chromatography.

| Sample | % Ethyl ester | % Monoglyceride | % Diglyceride | % Triglyceride |
|---|---|---|---|---|
| After enz. reaction | 57.0 | 34.2 | 6.7 | 0 |
| After EtOH removal | 59.5 | 32.4 | 5.7 | 0 |
| After distillation | 12.4 | 74.0 | 13.6 | 0 |

| Sample | Ester/glycerides ratio | Mono-:di-:triglyceride ratio |
|---|---|---|
| After enz. reaction | 58:42 | 84:16:0 |
| After EtOH removal | 61:39 | 85:15:0 |
| After distillation | 12:88 | 84:16:0 |

Example 13

Alcoholysis of Castor Oil 1.5 kg castor oil and 0.75 kg ethanol were weighed into a heatable double-jacketed reactor. 15 g water and 1.5 g Na$_2$CO$_3$ were added with stirring. The reaction was initiated by addition of 15 g Lipolase lipase and was carried out with stirring at room temperature. After 46 hours, the reaction was terminated and a sample was analyzed by gas chromatography. The reaction mixture was heated with stirring to 80° C. A vacuum was applied and the excess ethanol was evaporated from the reaction mixture. The reaction mixture was then expanded to normal pressure and 10 g Tonsil® and 6 g water were added. The mixture was stirred for 30 minutes at 80° C. and then for one hour in vacuo at 80° C. in order to remove residual water from the reaction mixture. After expansion of the reaction mixture to normal pressure, the mixture was filtered while warm. A sample was taken for analysis by gas chromatography.

| Sample | % Ethyl ester | % Monoglyceride | % Diglyceride | % Triglyceride |
|---|---|---|---|---|
| After enz. reaction | 59.7 | 33.4 | 5.7 | 0 |
| After EtOH removal | 58.8 | 30.0 | 8.9 | 0 |

| Sample | Ester/glycerides ratio | Mono-:di-:triglyceride ratio |
|---|---|---|
| After enz. reaction | 60:40 | 85:15:0 |
| After EtOH removal | 60:40 | 77:23:0 |

Example 14

Testing of the Emulsifying Effect of the Monoglycerides

The emulsifying property of the enzymatically-produced and distilled monoglycerides was tested in a system of 80% water and 20% oil. Myritol® 312 (medium chain triglyceride) and paraffin oil were used as the oils. A molecular-distilled monoglyceride (Monomuls® 90 O) with a monoglyceride content of >90% was used for comparison. The emulsifying properties in the Myritol 312/water system were determined at active substance concentrations of 1%, 2.5% and 5%. The emulsifying properties in the paraffin oil/water system were determined at active substance concentrations of 1% and 5%. The nature of the emulsion formed was determined by conductivity measurement. Tests were carried out with the monoglyceride mixtures of Examples 9, 10 and 11.

Emulsion Formation in the Myritol® 312/Water System

| Substance | Active substance | | | Emulsion type |
|---|---|---|---|---|
| | 1% | 2.5% | 5% | |
| Monoglyceride (Example 10) | No | Yes | Yes | W/O |
| Monoglyceride (Example 11) | No | No | Yes | W/O |
| Monoglyceride (Example 12) | No | No | Yes | W/O |
| Monomuls ® 90 O | No | Yes | Yes | W/O |

Emulsion Formation in the Paraffin Oil/Water System

| Substance | Active substance | | Emulsion type |
|---|---|---|---|
| | 1% | 5% | |
| Monoglyceride (Example 10) | Yes | Yes | W/O |
| Monoglyceride (Example 11) | Yes | Yes | W/O |
| Monoglyceride (Example 12) | Yes | Yes | W/O |
| Monomuls 90 O | Yes | Yes | W/O |

Result:

All the enzymatically-produced monoglycerides have good emulsifying properties. The monoglyceride produced from sunflower oil has comparable emulsifier properties to the molecular-distilled Monomuls 90 O. The monoglycerides produced from new sunflower oil and thistle oil have a somewhat weaker emulsifying effect which is probably attributable to the relatively high levels of ethyl ester still present.

Example 15

Testing of the Lubricating Properties in Diesel Fuel

The lubricating properties were subjected to an HFFR test (high-frequency reciprocating rig test) by CEC method F-06T-94. Various diesel fuels and monoglyceride mixtures based on sunflower oil and rapeseed oil, as shown in the following Table, were used.

| Number | Sample | Raw material |
|---|---|---|
| Sample 1 | Monoglyceride/ethyl ester mixture | Sunflower oil |
| Sample 2 | Monoglyceride mixture distilled | Rapeseed oil |
| Sample 3 | Monoglyceride/butyl ester mixture | Rapeseed oil |

| | Ester | Monoglyceride | Diglyceride | Triglyceride |
|---|---|---|---|---|
| Sample 1 | 56.0 | 27.8 | 12.8 | <1 |
| Sample 2 | 3.5 | 61.0 | 32.0 | 2.5 |
| Sample 3 | 66.0 | 21.5 | 9.0 | <1 |

Results:

| Number | Concentration in diesel | HFFR value | Film |
|---|---|---|---|
| Diesel A | Blank | 411 μm | 19 μm |
| Sample 1 | 200 ppm | 261 μm | 67 μm |
| Diesel B | Blank | 542 μm | 20 μm |
| Sample 1 | 100 ppm | 311 μm | 65 μm |
| Sample 1 | 150 ppm | 217 μm | 70 μm |
| Sample 1 | 200 ppm | 231 μm | 68 μm |
| Diesel C | Blank | 615 μm | |
| Sample 2 | 100 ppm | 183 μm | |
| Sample 2 | 300 ppm | 170 μm | |
| Sample 3 | 100 ppm | 279 μm | |
| Sample 3 | 300 ppm | 195 μm | |

Result:

All samples significantly improve the lubricating properties of the diesel fuels used and reduce the HFFR values to below prescribed limits (for example, currently 450 μm in Switzerland).

Example 16

Analysis of the Fatty Acid Composition of the Monoglyceride from Sunflower Oil

After complete methylation with TMSH in dichloromethane, the monoglyceride fraction and the distillate fraction from Example 10 were analyzed for their fatty acid composition by gas chromatography and compared with the starting material, sunflower oil.

Result:

| | % Sunflower oil | % Monoglyceride | % Distillate |
|---|---|---|---|
| Palmitic acid | 6.2 | 1.3 | 9.8 |
| Stearic acid | 3.4 | 1.0 | 3.5 |
| Oleic acid | 25.4 | 23.3 | 25.3 |
| Linoleic acid | 65.0 | 74.4 | 61.4 |

Result:

The monoglyceride fraction shows an enrichment of linoleic acid and a serious depletion of the saturated fatty acids by comparison with the starting product.

The invention claimed is:

1. A process for the production of monoglycerides, comprising the step of reacting one or more triglycerides with one or more linear or branched C1-C8 alcohols, in the presence of an esterase which is activated by the addition of one or more alkaline salts, wherein said esterase is not immobilized, and wherein said reaction occurs in the absence of organic solvents other than said alcohols.

2. The process according to claim 1, further comprising the step of deactivating said esterase.

3. The process according to claim 1, wherein the process is carried out at a temperature in the range of 10° C. to 40° C., with a water content of 0.1 to 10% by weight, based on the quantity of triglyceride.

4. The process according to claim 1, wherein said esterase originates from organisms selected from the group consisting of *Thermomyces lanugenosus, Candida antarctica A, Candida antarctica B, Rhizomucor miehei, Candida cylindracea, Rhizopus javanicus, Porcine pancreas, Aspergillus niger, Candida rugosa, Mucor javanicus, Pseudomonas fluorescens, Rhizopus oryzae, Pseudompnas* sp., *Chromobacterium viscosum, Fusarium oxysporum* and *Penicilium camemberti*.

5. The process according to claim 1, wherein said esterase comprises a lipase.

6. The process according to claim 5, wherein said lipase comprises a 1,3-specific lipase.

7. The process according to claim 5, wherein said lipase is from *Thermomyces lanugenosus*.

8. The process according to claim 1, wherein said esterase is present in quantities of from 0.05 to 2% of the commercially-obtained liquid preparation, based on the quantity of triglyceride.

9. The process according to claim 1, wherein the alkaline inorganic salts for activating said esterase are selected from the group consisting of hydroxides, carbonates and phosphates, of sodium, potassium, calcium, magnesium and ammonium, predissolved in water.

10. The process according to claim 1 wherein the alkaline inorganic salts for activating said esterase are added in quantities of from 0.00001 to 1% by weight, based on the quantity of triglyceride.

11. The process according to claim 1, wherein said triglycerides comprise triglycerides from fats and oils which have a high percentage content of mono- and/or polyunsaturated fatty acids, selected from the group consisting of sunflower oil, rapeseed oil, thistle oil, soybean oil, linseed oil, peanut oil, tallows, olive oil, castor oil, palm oil and old oils.

12. The process according to claim 1, wherein said alcohols comprise ethanol and/or 1-propanol, and the alcohol content is 10 to 75% by weight, based on the triglyceride.

13. The process according to claim 1, further comprising the step of removing said alcohols by distillation.

14. A process for the production of monoglycerides, comprising the steps of:
   (1) reacting one or more triglycerides with one or more linear or branched C1-C8 alcohols, in the presence of an esterase which is activated by the addition of one or more alkaline salts, and
   (2) separating the remaining triglycerides and any by-product diglycerides from the monoglycerides by distillation, wherein said esterase is not immobilized, and wherein said reaction occurs in the absence of organic solvents other than said alcohols.

* * * * *